(12) United States Patent
Galloway

(10) Patent No.: US 11,382,791 B2
(45) Date of Patent: Jul. 12, 2022

(54) DRUG DELIVERY DEVICE AND APPLICATIONS OF SAME

(71) Applicant: Vanderbilt University, Nashville, TN (US)

(72) Inventor: Robert L. Galloway, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 749 days.

(21) Appl. No.: 15/751,586

(22) PCT Filed: Oct. 24, 2016

(86) PCT No.: PCT/US2016/058410
§ 371 (c)(1),
(2) Date: Feb. 9, 2018

(87) PCT Pub. No.: WO2017/035544
PCT Pub. Date: Mar. 2, 2017

(65) Prior Publication Data
US 2020/0229968 A1    Jul. 23, 2020

Related U.S. Application Data

(60) Continuation-in-part of application No. 14/060,963, filed on Oct. 23, 2013, now Pat. No. 10,610,406, and (Continued)

(51) Int. Cl.
*A61F 9/007* (2006.01)
*A61F 9/008* (2006.01)
(Continued)

(52) U.S. Cl.
CPC ............ *A61F 9/007* (2013.01); *A61B 1/3132* (2013.01); *A61B 5/064* (2013.01); *A61B 5/065* (2013.01);
(Continued)

(58) Field of Classification Search
CPC combination set(s) only.
See application file for complete search history.

(56) References Cited

U.S. PATENT DOCUMENTS 6,592,545 B1    7/2003    Bellhouse et al.
2005/0014995 A1    1/2005    Amundson et al.
(Continued)

FOREIGN PATENT DOCUMENTS

EP    0589379 A1    3/1994

OTHER PUBLICATIONS

Korean Intellectual Property Office (ISR/KR), "International Search Report for PCT/US2016/058410", Korea, dated Mar. 6, 2017.

*Primary Examiner* — Scott Luan
(74) *Attorney, Agent, or Firm* — Locke Lord LLP; Tim Tingkang Xia, Esq.

(57) ABSTRACT

A drug delivery device includes a catheter; a retention cap attached to an end of the catheter, having an operably openable surface; a flexible membrane having a rim securely connected to an inner surface of the catheter to define a first volume and a second volume therein, such that the second volume is substantially the same as a desired drug volume; and a pressurizable member coupled to the catheter. In use, the desired drug volume is preloaded into the second volume of the catheter that in turn is slided into a guidance device, when the guidance device is placed in a target, the pressurizable member applies a pressure into the first volume to exert a force upon the flexible membrane to operably squeeze the second volume, which in turn pressurizes the operably openable surface of the retention cap to open, thereby unloading the desired drug volume into the target.

31 Claims, 4 Drawing Sheets

Related U.S. Application Data a continuation-in-part of application No. 13/848,505, filed on Mar. 21, 2013, now abandoned, which is a division of application No. 10/895,635, filed on Jul. 21, 2004, now Pat. No. 8,403,828.

(60) Provisional application No. 62/209,203, filed on Aug. 24, 2015, provisional application No. 61/717,376, filed on Oct. 23, 2012, provisional application No. 60/488,758, filed on Jul. 21, 2003.

(51) Int. Cl.
| | | |
|---|---|---|
| *A61B 5/06* | (2006.01) | |
| *A61B 1/313* | (2006.01) | |
| *A61B 34/20* | (2016.01) | |
| *A61B 34/10* | (2016.01) | |
| *A61B 1/012* | (2006.01) | |
| *A61B 90/00* | (2016.01) | |

(52) U.S. Cl.
CPC .............. *A61B 34/20* (2016.02); *A61F 9/008* (2013.01); *A61F 9/00802* (2013.01); *A61F 9/00821* (2013.01); *A61B 1/012* (2013.01); *A61B 90/361* (2016.02); *A61B 2034/107* (2016.02); *A61B 2034/2051* (2016.02); *A61B 2034/2055* (2016.02); *A61B 2034/2072* (2016.02); *A61F 2009/00851* (2013.01); *A61F 2009/00897* (2013.01)

(56) References Cited

U.S. PATENT DOCUMENTS

2007/0088247 A1    4/2007    Bliweis et al.
2014/0051972 A1    2/2014    Galloway et al.

DRUG DELIVERY DEVICE AND APPLICATIONS OF SAME

CROSS-REFERENCE TO RELATED PATENT APPLICATIONS

This PCT application claims priority to and the benefit of U.S. Provisional Patent Application Ser. No. 62/209,203, filed Aug. 24, 2015, entitled "DRUG DELIVERY DEVICE AND APPLICATIONS OF SAME," by Robert L. Galloway. The disclosures of the above application is incorporated herein in its entirety by reference.

This PCT application is also a continuation-in-part application of U.S. patent application Ser. No. 14/060,963, filed Oct. 23, 2013, entitled "DRUG DELIVERY DEVICE AND APPLICATIONS OF SAME", by Robert Galloway et al., which itself claims priority to and the benefit of, pursuant to 35 U.S.C. § 119(e), U.S. Provisional Patent Application Ser. No. 61/717,376, filed Oct. 23, 2012, entitled "TRANS-ORBITAL DRUG ALIQUOT DELIVERY DEVICE AND APPLICATIONS OF SAME," by Robert Galloway et al. The disclosures of the above applications are incorporated herein in their entireties by reference.

This PCT application is also a continuation-in-part application of U.S. patent application Ser. No. 13/848,505, filed Mar. 21, 2013, entitled "OPHTHALMIC ORBITAL SURGERY APPARATUS AND METHOD AND IMAGE-GUIDED NAVIGATION SYSTEM", by Louise A. Mawn et al., which itself is a divisional application of U.S. patent application Ser. No. 10/895,635, filed Jul. 21, 2004, entitled "OPHTHALMIC ORBITAL SURGERY APPARATUS AND METHOD AND IMAGE-GUIDED NAVIGATION SYSTEM", by Louise A. Mawn et al., now U.S. Pat. No. 8,403,828, which itself claims priority to and the benefit of, pursuant to 35 U.S.C. § 119(e), U.S. Provisional Patent Application Ser. No. 60/488,758, filed Jul. 21, 2003, entitled "OPHTHALMIC ORBITAL SURGERY APPARATUS AND METHOD AND IMAGE-GUIDED NAVIGATION SYSTEM", by Louise A. Mawn et al., The disclosures of the above applications are incorporated herein in their entireties by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The invention relates generally to surgery and medication, and more particularly to a drug delivery device and applications of the same in an image-guided surgery.

BACKGROUND OF THE INVENTION

With the growth of image-guided interventions, it is getting better at guiding devices right to where the treatment needs to be applied. To date that has been resection or ablation. But a number of treatments require the delivery of an exact aliquot of a fluid such as chemotherapy, drug antibiotic, gene therapy, and so on, to a target of interest. The problem, however, is that the target is remote from the hands of the interventionalist. A long needle or tube has usually been used to deliver the fluid to the target, but there is a dead space within the needle or tube that wastes expensive materials. The longer the needle or tube is, the greater the dead space of wasted material is. Further, the needle or tube is tough to guide. In addition, the delivered amount of the fluid may be unknown. To control the amount of the fluid delivered from a drug delivery system, a flow regulator is usually utilized between the fluid reservoir and the target to regulate a flow rate of the fluid to the target. However, the use of the flow regulator unavoidably increases the design complexity, operative difficulty and cost of the drug delivery system.

Therefore, a heretofore unaddressed need exists in the art to address the aforementioned deficiencies and inadequacies.

SUMMARY OF THE INVENTION

This invention addresses unmet needs in the current clinical practice, for example, in the area of treatments of nerve diseases and other diseases. Drug delivery using drops or injections at acceptable doses suffer from inadequacy of the drug dose actually reaching the nerve.

In one aspect, the invention relates to a drug delivery device for delivering a desired volume of a drug into a target of interest of a human or an animal. In one embodiment, the drug delivery device includes a catheter having a first end and an opposite, second end, being slidable into a guidance device; a retention cap attached to the second end of the catheter, having an operably openable surface and a hinge; a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable; and a pressurizable member coupled to the catheter for operably changing the first volume and the second volume of the catheter. The drug delivery device is devoid of a flow regulator for regulating a flow of the desired volume of the drug into the target of interest.

In use, the desired volume of the drug is preloaded into the second volume of the catheter that in turn is slided into the guidance device, and when the guidance device is placed in the target of interest, the pressurizable member applies a pressure into the first volume of the catheter to exert a force upon the flexible membrane so as to operably reduce the second volume of the catheter, which in turn pressurizes the operably openable surface of the retention cap to open, thereby unloading the desired volume of the drug into the target of interest.

In one embodiment, the first volume of the catheter is filled with fluid comprising benign gas or liquid. In one embodiment, the fluid comprises saline.

In one embodiment, the catheter is rigid or flexible.

In one embodiment, the flexible membrane is made of an elastic material that is compatible with both the fluid in the first volume and the preloaded drug in the second volume.

In one embodiment, the flexible membrane is impermeable to both the fluid in the first volume and the preloaded drug in the second volume.

In one embodiment, the retention cap has an operable opening defined when the operably openable surface is operably opened and hinged at the hinge. In one embodiment, the operably opening has a diameter that is substantially the same as an inner diameter of the catheter.

In one embodiment, the retention cap has an trough that is either molded or cut into its surface to define the operably openable surface and the hinge.

In one embodiment, the retention cap is attached to an outer surface of the second end of the catheter, or an inner surface of the second end of the catheter.

In one embodiment, the pressurizable member comprises a syringe coupled to the first end of the catheter and being in a fluid communication with the first volume of the catheter.

In one embodiment, the guidance device comprises an endoscope.

In addition, the drug delivery device may be disposable or re-useable.

In another aspect, the invention relates to a method for delivering a desired volume of a drug into a target of interest of a human or an animal. In one embodiment, the method includes providing a drug delivery device.

The drug delivery device has a catheter having a first end and an opposite, second end; a retention cap attached to the second end of the catheter, having an operably openable surface and a hinge; a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable; and a pressurizable member coupled to the first end of the catheter for operably changing the first volume and the second volume of the catheter.

Further, the method includes preloading the desired volume of the drug into the second volume of the catheter; placing the second end of the catheter in the target of interest; and applying a pressure onto the first volume of the catheter to exert a force upon the flexible membrane so as to operably reduce the second volume of the catheter, which in turn pressurizes the operably openable surface of the retention cap to open, thereby unloading the desired volume of the drug into the target of interest.

In a further aspect, the invention relates to an endoscope. In one embodiment, the endoscope has a probe housing having a proximal end, a distal end and a lumen extending between the proximal end and the distal end; at least one image fiber disposed in the lumen that communicates image information from the distal end of the probe; and a drug delivery device for delivering a desired volume of a drug into a target of interest; and an access conduit disposed in the lumen that receives an ablation instrument or a coagulating instrument for performing a surgical procedure.

The drug delivery device includes a catheter disposed in the lumen, having a first end close to the proximal end of the probe, and an opposite, second end close to the distal end of the probe; a retention cap attached to the second end of the catheter, having an operably openable surface and a hinge; a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable, wherein the desired volume of the drug is preloaded into the second volume of the catheter; and a pressurizable member coupled to the first end of the catheter for operably unloading the desired volume of the drug into the target of interest. The drug delivery device is devoid of a flow regulator for regulating a flow of the desired volume of the drug into the target of interest.

In one embodiment, the first volume of the catheter is filled with fluid comprising benign gas or liquid.

In one embodiment, the flexible membrane is made of an elastic material that is compatible with both the fluid in the first volume and the preloaded drug in the second volume.

In one embodiment, the flexible membrane is impermeable to both the fluid in the first volume and the preloaded drug in the second volume.

In one embodiment, the retention cap has an operable opening defined when the operably openable surface is operably opened and hinged at the hinge. In one embodiment, the operably opening has a diameter that is substantially the same as an inner diameter of the catheter.

In one embodiment, the retention cap has an trough that is either molded or cut into its surface to define the operably openable surface and the hinge.

In one embodiment, the retention cap is attached to an outer surface of the second end of the catheter, or an inner surface of the second end of the catheter.

In one embodiment, the pressurizable member comprises a syringe coupled to the first end of the catheter and being in a fluid communication with the first volume of the catheter. During the surgical procedure, the pressurizable member applies a pressure into the first volume of the catheter to exert a force upon the flexible membrane so as to operably reduce the second volume of the catheter, which in turn pressurizes the operably openable surface of the retention cap to open, thereby unloading the desired volume of the drug into the target of interest.

In one embodiment, the endoscope further includes a magnetic tracking tip disposed proximate the distal end of the probe housing and configured to generate magnetic tracking tip location data identifying a location of the distal end of the probe housing.

In addition, the endoscope may further include a purge fluid/gas port disposed at the proximal end of the flexible probe that accepts purge fluid/gas; and a purge fluid/gas conduit disposed in the lumen and in fluid communication with the purge fluid/gas port, the conduit delivering purge fluid/gas to the distal end of the endoscope.

In one embodiment, the ablation instrument is a laser delivery system comprising a waveguide disposed in the lumen; a laser source coupled to a proximal end of the waveguide; and a lens mounted to a distal end of the waveguide nearest the distal end of the endoscope. The laser source is one of a free electron laser source, an Argon laser source, a Dye laser source, a YAG laser source and a carbon dioxide laser source.

In another embodiment, the ablation instrument uses one of radio-frequency waves, microwaves, ultrasonic waves, infrared waves, heat, cryoablation, and a laser to ablate the particular portion of the tissue.

In one embodiment, the coagulating instrument uses one of radio-frequency waves, microwaves, ultrasonic waves, infrared waves, heat, cryoablation and a laser.

In yet another aspect, the invention relates to a method for performing an image-guided surgical procedure with an instrument in a target of interest of a human or an animal and delivering a desired volume of a drug therein during the image-guided surgical procedure.

In one embodiment, the method includes guiding an endoscope into the target of interest. The endoscope comprises a probe housing having a proximal end, a distal end and a lumen extending between the proximal end and the distal end; at least one image fiber disposed in the lumen that communicates image information from the distal end of the probe; a drug delivery device; an access conduit disposed in the lumen that receives the instrument; and a magnetic tracking tip disposed proximate the distal end of the probe housing and configured to generate magnetic tracking tip location data identifying a location of the distal end of the probe housing.

The drug delivery device has a catheter disposed in the lumen, having a first end close to the proximal end of the probe, and an opposite, second end close to the distal end of the probe; a retention cap attached to the second end of the catheter, having an operably openable surface and a hinge; a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable, wherein the desired volume of the drug is preloaded into the second volume of the catheter; and a pressurizable member coupled to the first end of the catheter for operably unloading the desired volume of the drug into the target of interest.

Further, the method also includes detecting the magnetic tracking tip in a three dimensional (3D) physical space; obtaining an image space having a plurality of tomographic images each containing all image information; determining point-based registrations mapping the 3D physical space to the image space based on points in the 3D physical space and corresponding points in the image space; determining a location and an orientation of the instrument in the image space based on the magnetic tracking tip location data generated by the magnetic tracking tip in the 3D physical space and the point-based registrations, so as to perform the image-guided surgical procedure; dynamically displaying, while performing the image-guided surgical procedure, a selected one of the plurality of the tomographic images that overlaps the location of the instrument in the image space and indications of the location and orientation of the instrument in the image space; and applying a pressure onto the first volume of the catheter of the endoscope to exert a force upon the flexible membrane so as to operably reduce the second volume of the catheter, which in turn pressurizes the operably openable surface of the retention cap to open, thereby unloading the desired volume of the drug into the target of interest.

Moreover, the method may also include scanning tissue of the human or the animal to acquire, store and process a 3D reference of tissue prior to the tissue being surgically exposed, so as to create a triangularized mesh based on the scanned tissue, determine the volumetric center of a particular portion of the tissue to be ablated, coagulated or medicated during the surgery, and implement an algorithm using the triangularized mesh and the physical space data collected by the instrument to determine the point-based registrations.

In one embodiment, the image-guided surgical procedure is performed by transmitting a free electron laser (FEL) to surgically ablate a particular portion of a tissue.

In one embodiment, the magnetic tracking tip location data comprises {x, y, z} positional coordinates and orientation angles and a rotation matrix, wherein the image space comprises scanned images that are preoperatively obtained.

In yet a further aspect, the invention relates to an apparatus for performing an image-guided surgical procedure with an instrument in a target of interest of a human or an animal and delivering a desired volume of a drug therein during the image-guided surgical procedure. In one embodiment, the apparatus includes an endoscope, a magnetic tracking system and an image data processor.

In one embodiment, the endoscope comprises a probe housing having a proximal end, a distal end and a lumen extending between the proximal end and the distal end; at least one image fiber disposed in the lumen that communicates image information from the distal end of the probe; a drug delivery device; an access conduit disposed in the lumen that receives the instrument; and a magnetic tracking tip disposed proximate the distal end of the probe housing and configured to generate magnetic tracking tip location data identifying a location of the distal end of the probe housing.

The drug delivery device has a catheter disposed in the lumen, having a first end close to the proximal end of the probe, and an opposite, second end close to the distal end of the probe; a retention cap attached to the second end of the catheter, having an operably openable surface and a hinge; a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable, wherein the desired volume of the drug is preloaded into the second volume of the catheter; and a pressurizable member coupled to the first end of the catheter for operably unloading the desired volume of the drug into the target of interest.

In one embodiment, during the image-guided surgical procedure, the pressurizable member applies a pressure into the first volume of the catheter to exert a force upon the flexible membrane so as to operably reduce the second volume of the catheter, which in turn pressurizes the operably openable surface of the retention cap to open, thereby unloading the desired volume of the drug into the target of interest.

In one embodiment, the magnetic tracking system is configured to detect the magnetic tracking tip in a 3D physical space.

In one embodiment, the image data processor is configured to obtain an image space having a plurality of tomographic images each containing all image information; determine point-based registrations mapping the 3D physical space to the image space based on points in the 3D physical space and corresponding points in the image space; determine a location and an orientation of the instrument in the image space based on magnetic tracking tip location data generated by the magnetic tracking tip in the 3D physical space and the point-based registrations; and dynamically display, while performing the image-guided surgical procedure, a selected one of the plurality of the tomographic images that overlaps the location of the instrument in the image space and indications of the location and orientation of the instrument in the image space.

In one embodiment, the instrument is configured to transmit an FEL that surgically ablates a particular portion of a tissue, and comprises a laser delivery system including a waveguide and a lens mounted to a distal end of the waveguide adjacent to the distal end of the endoscope, wherein a proximal end of the waveguide is coupled to a laser source.

In one embodiment, the magnetic tracking tip location data comprises {x, y, z} positional coordinates and orientation angles and a rotation matrix, wherein the image space comprises scanned images that are preoperatively obtained, wherein the image data processor provides the scanned images for display while the image-guided surgery is being performed.

In one embodiment, the apparatus further includes a scanning device for scanning tissue of the patient to acquire, store and process a 3D reference of tissue prior to the tissue being surgically exposed, wherein the image data processor creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
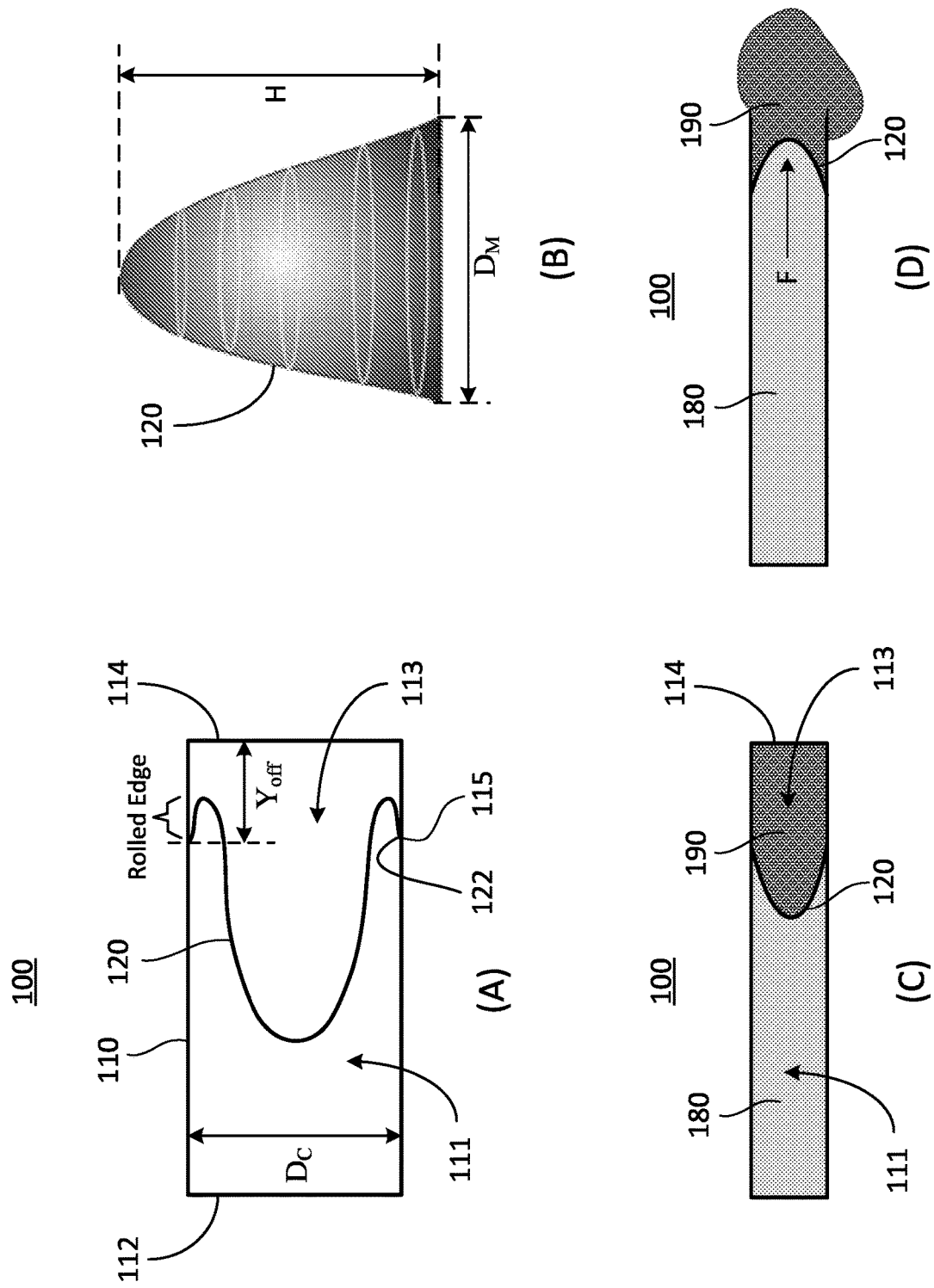
FIG. 1 shows schematically a drug delivery device according to one embodiment of the invention, (A) a section view, (B) a parabolic solid volume structure formed by a flexible membrane, (C) a section view with a desired volume of a drug preloaded, and (D) a section view with the desired volume of a drug delivered.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about" "substantially" or "approximately" can be inferred if not expressly stated.

The description will be made as to the embodiments of the invention in conjunction with the accompanying drawings. In accordance with the purposes of this invention, as embodied and broadly described herein, this invention, in one aspect, relates to a drug delivery device and applications of the same in an image-guided surgery.

This invention addresses unmet needs in the current clinical practice, for example, in the area of treatments of, but not limited to, nerve diseases. Drug delivery using drops or injections at acceptable doses suffer from inadequacy of the drug dose actually reaching the nerve. Accordingly, the invention is directed to a trans-orbital drug aliquot delivery device having a catheter that is slidable down a guidance device, such as down the working channel of an endoscope. The catheter has a first end and an opposite, second end (a distal end), where the second end defines an opening having a diameter that is the same as an inner diameter of the catheter. At a distance from the distal end of the catheter, there is a flexible membrane having a rim, like a tiny condom, connected to the inner surface of the catheter to define a chamber (reservoir). By attaching the flexible membrane that forms the chamber in such a manner when inverting it stops at the distal end of the catheter. There is a relationship between a desired delivery volume of a drug and the position of the membrane rim (the condom rim) such that the volume of the chamber defined by the membrane and the distal end of the catheter is substantially the same as the desired delivery volume. On the other side of the membrane (the condom) the catheter is filled with saline. A saline filled syringe is connected onto the proximal end of the catheter. In use, the catheter is slided into a position and the syringe is pushed. The exact control of the syringe is not necessary since the delivery volume is controlled by the preload. Therefore, there is no need to have a flow regulator for regulating a flow of the drug delivered into the target of interest. The saline pushes the membrane (the condom) which inverts, delivering the drug load. In other words, by creating a catheter with a flexible reservoir of a known volume at the distal end (patient end) and using a benign material such as isotonic saline to invert that reservoir, an exact amount of a drug can be delivered. The drug can be any type of pharmaceutical agents for medication and/or diagnosis.

Figure 2:
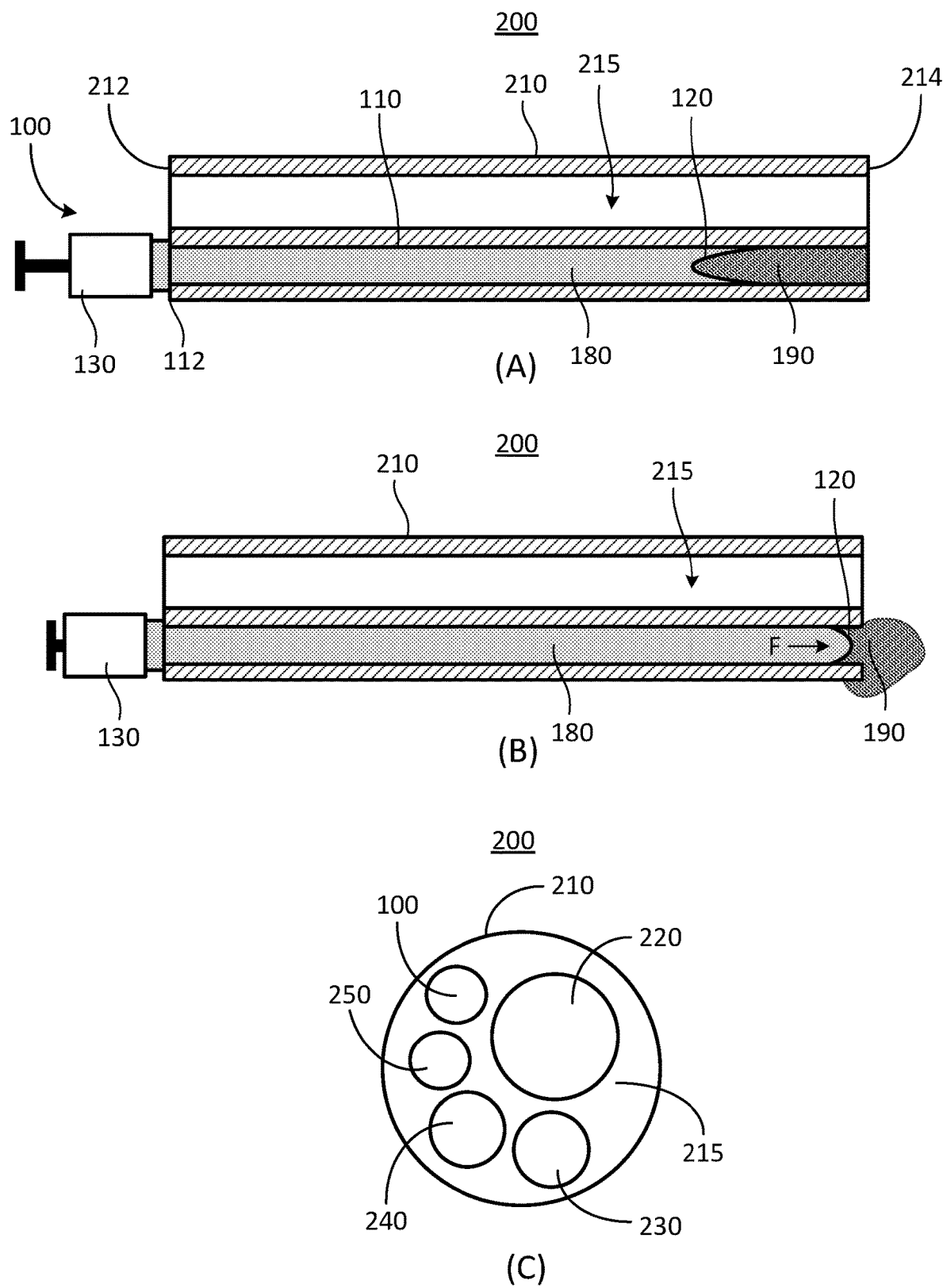
FIG. 2 shows schematically an endoscope having the trans-orbital drug delivery device of FIG. 1, according to one embodiment of the invention, (A) a section view with a desired volume of a drug preloaded, (B) a section view with the desired volume of a drug delivered, and (C) another section view.

Specifically, FIGS. 1 and 2 shows schematically a trans-orbital drug delivery device 100 for delivering a desired volume of a drug into a target of interest of a human or an animal according to one embodiment of the invention. In the exemplary embodiment, the drug delivery device 100 includes a catheter 110 having a first end (proximal end) 112 and an opposite, second end (distal end) 114, as shown in FIGS. 1A, 1C and 1D. The catheter 110 is a rigid or flexible cylinder with a circular open cross-section, and is configured to be slidable into a guidance device 200, such as an endoscope.

Further, the drug delivery device 100 has a flexible membrane 120 having a rim 122 securely connected/attached to an inner surface of the catheter 110 at a position 115 proximal to the second end 114 of the catheter 110 to define a first volume 111 inside the catheter 110 between the first end 112 and the flexible membrane 120, and a second volume 113 inside the catheter 110 between the flexible membrane 120 and the second end 114, as shown in FIGS. 1A-1D. The second volume 113 of the catheter 110 is substantially the same as the desired volume of the drug. Since the membrane 120 is flexible, the first volume 111 and the second volume 113 are operably and complementarily changeable. For example, if a force, F, toward the second end 114 is exerted on the flexible membrane 120, the first volume 111 becomes larger, while the second volume 113 becomes smaller (i.e., being squeezed), as shown in FIG. 1D. In other words, the second volume 113 can be squeezed (or inverted) by applying a force on the flexible membrane 120.

In one embodiment, the flexible membrane 120 is a parabolic, flexible membrane. The second volume 113 forms a parabolic solid volume structure having a diameter $D_M$, and a height, H, as shown in FIG. 1B The drug delivery device 100 is constructed by providing the catheter 110 with a diameter $D_C$ and placing the membrane edge (or rim) 122 of the parabolic, flexible membrane 120 of the diameter $D_M$ into at a position 115 proximal to the distal end 114 of that catheter 110. $D_M$ is greater than $D_C$. The membrane 120 is placed with the membrane edge (or rim) 122 rolled under at a distance $(D_M-D_C)/2$ and attached to the wall (inner surface) of the catheter 110 either by glue or thermal bonding.

The position 115 has a distance $Y_{off}$ from the distal end 114 of the catheter 110. $Y_{off}$ is determined by a distance such the membrane 120, when inverted, does not extend beyond the tip of the distal end 114 of the catheter 110.

With the parabolic membrane 120 pulled toward the proximal end 112 of the catheter 110, the preload (the desired volume of the drug) 190 is loaded into the second volume 113 from the distal end 114 of the catheter 110. The preload volume is defined as PV, which is maximally equal to $$PV = \pi * D_C * Y_{off} + (\pi/2) * H * (D_C/2)^2.$$

In one embodiment, the preload volume is protected by placing an adhesive cover over the distal end 114 of the catheter 110.

Figure 4:
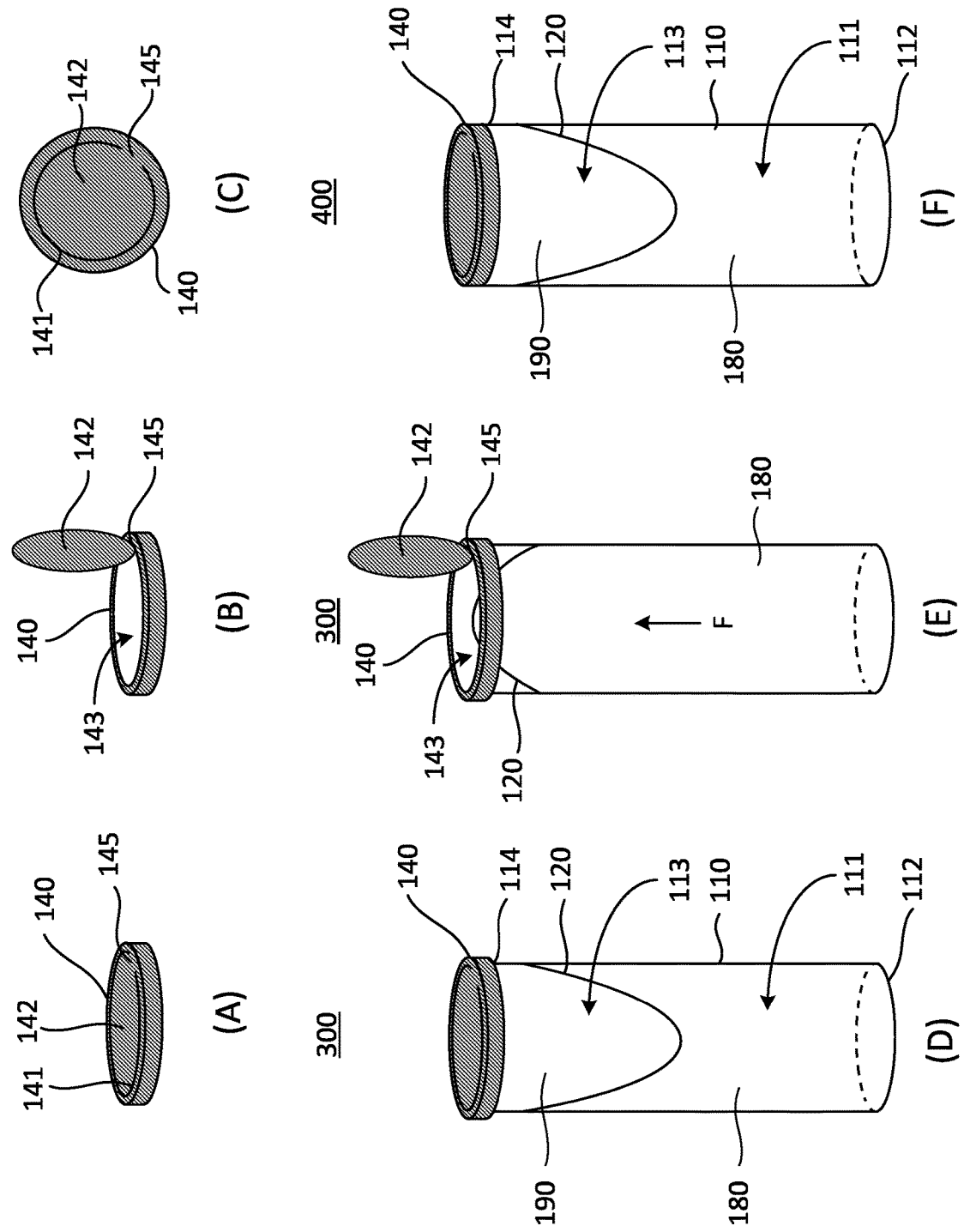
FIG. 4 shows schematically a drug delivery device according to embodiments of the invention, (A)-(C) perspective views and top view of a retention cap, and (D)-(F) perspective views of different embodiments of the drug delivery device.

In another embodiment, the preload volume is protected by placing a retention cap 140 disposed at the distal end 114 of the catheter 110. The details of the retention cap in one embodiment is shown in FIG. 4 and described below.

The first volume 111 of the catheter 110 is filled with fluid 180 comprising benign gas or liquid, such as saline or the like.

In one embodiment, the flexible membrane 120 is made of an elastic material that is compatible with both the fluid 180 in the first volume 111 and the preloaded drug 190 in the second volume 113. Further, the flexible membrane 120 is impermeable to both the fluid 180 in the first volume 111 and the preloaded drug 190 in the second volume 113.

As shown in FIG. 2, the drug delivery device 100 also has a pressurizable member 130 coupled to the catheter 110 for operably changing the first volume 111 and the second volume 113 of the catheter 110. In the exemplary embodiment, the pressurizable member 130 includes a syringe coupled to the first end 112 of the catheter 110 and being in a fluid communication with the first volume 112 of the catheter 110. It should be noted that other types of the pressurizable members, such as pumps or the like, can also be utilized to practice the invention.

In use, when the preload volume (i.e., preloaded volume of the drug) 190 is to be deployed, the adhesive cover is removed and the catheter 110 is slided into a guidance device such as an endoscope 200 that is guided to the desired preload location, i.e., the target of interest. Surface tension should hold the delivery fluid in the catheter 110, as shown in FIGS. 1C and 2A. The pressurizable member 130 applies a pressure into the first volume 111 of the catheter 110 to exert a force upon the flexible membrane 120 so as to operably squeeze the second volume 113 of the catheter 110, which causes the flexible membrane 120 to invert and extrude the preload 190, i.e., unloading the desired volume of the drug 190 into the target of interest, as shown in FIGS. 1D and 2B.

It is expected that not all of the preload volume will be delivered. This should be a function of the parabolic membrane not completely filling the distal end of the catheter once deployed and the viscosity of the preload material. However, this should be deterministic which means that the delivered volume (DV) from any given configuration can be calibrated so that exact volume delivery can occur.

The drug delivery device 100 may be disposable or re-useable.

As disclosed above, no flow regulator is needed, since the amount of the drug delivered is known. In other words, the drug delivery device 110 according to embodiments of the invention is devoid of a flow regulator for regulating a flow of the desired volume of the drug into the target of interest, which makes the device design simple, improves the operability and reduces the cost.

Another aspect of the invention, a method for delivering a desired volume of a drug into a target of interest of a human or an animal includes providing a drug delivery device as disclosed above and shown in FIGS. 1 and 2; preloading the desired volume of the drug into the second volume of the catheter; placing the second end of the catheter in the target of interest; and applying a pressure onto the first volume of the catheter to exert a force upon the flexible membrane so as to operably reduce the second volume of the catheter, thereby unloading the desired volume of the drug into the target of interest.

As shown in FIG. 2, the invention is also directed to a novel image guided endoscope 200 that utilizes the above-disclosed drug delivery device 100, which can be introduced in a trans-orbital fashion to a location adjacent to the optic nerve. This would facilitate the controlled delivery of a very small aliquot of a pharmaceutical agent right at the location needed, namely next to the optic nerve.

The endoscope 200 has a probe housing 210 having a proximal end 212, a distal end 214, and a lumen 215 extending between the proximal end 212 and the distal end 214, an image fiber or fiber bundle 220 disposed in the lumen 215 that communicates image information from the distal end 214 of the probe 210, and a drug delivery device 100 for delivering a desired volume of a drug 190 into a target of interest, and an access conduit 230 disposed in the lumen 215 that receives an ablation instrument or a coagulating instrument for performing a surgical procedure. The drug delivery device 100 is disclosed above and shown in FIG. 1, whose details will not be repeated herein.

The endoscope 200 also includes a magnetic tracking tip 240 disposed proximate the distal end of the probe housing and configured to generate magnetic tracking tip location data identifying a location of the distal end of the probe housing.

In addition, the endoscope 200 may further include a purge fluid/gas port disposed at the proximal end of the flexible probe that accepts purge fluid/gas; and a purge fluid/gas conduit 250 disposed in the lumen 215 and in fluid communication with the purge fluid/gas port, the conduit delivering purge fluid/gas to the distal end of the endoscope.

In one embodiment, the ablation instrument is a laser delivery system comprising a waveguide disposed in the lumen; a laser source coupled to a proximal end of the waveguide; and a lens mounted to a distal end of the waveguide nearest the distal end of the endoscope. The laser source is one of a free electron laser source, an Argon laser source, a Dye laser source, a YAG laser source and a carbon dioxide laser source.

In another embodiment, the ablation instrument uses one of radio-frequency waves, microwaves, ultrasonic waves, infrared waves, heat, cryoablation, and a laser to ablate the particular portion of the tissue.

In one embodiment, the coagulating instrument uses one of radio-frequency waves, microwaves, ultrasonic waves, infrared waves, heat, cryoablation and a laser.

Except the drug delivery device 100, the other parts of the endoscope 200 are substantially the same as that of the endoscope disclosed in U.S. patent application Ser. No. 13/848,505, which is incorporated herein in its entirety by reference, and the details of them will not be repeated herein.

For such an endoscope 200, during or after the surgical procedure, when a pressure is applied, by the pressurizable member 130 of the drug delivery device 100, into the first volume 111 of the catheter 110 to exert a force upon the flexible membrane 120, it operably squeeze the second volume 113 of the catheter 110, and causes the flexible membrane 120 to invert, which extrudes the desired volume of the drug into the target of interest.

According to the invention, the endoscope catheter is filled with saline and has a flexible membrane at the end that (upon application of pressure at syringe end) can release a precise amount of drug at the specific location with low pressure. The trans-orbital delivery of drugs can be conducted locally at the optical nerve using a tracked endoscope, preferably, a magnetically tracked endoscope. Additionally, this design facilitates the use of a very small, pre-determined amount of the drug and prevents wastage of costly drugs within the entire length of catheter.

In one aspect, the invention relates to a method for performing an image-guided surgical procedure with an instrument in a target of interest of a human or an animal and delivering a desired volume of a drug therein during the image-guided surgical procedure.

The method includes guiding an endoscope into the target of interest. The details of the endoscope are described above and will not be repeated herein.

Further, the method also includes detecting the magnetic tracking tip in a three dimensional (3D) physical space; obtaining an image space having a plurality of tomographic images each containing all image information; determining point-based registrations mapping the 3D physical space to the image space based on points in the 3D physical space and corresponding points in the image space; determining a location and an orientation of the instrument in the image space based on the magnetic tracking tip location data generated by the magnetic tracking tip in the 3D physical space and the point-based registrations, so as to perform the image-guided surgical procedure; dynamically displaying, while performing the image-guided surgical procedure, a selected one of the plurality of the tomographic images that overlaps the location of the instrument in the image space and indications of the location and orientation of the instrument in the image space; and applying a pressure onto the first volume of the catheter of the endoscope to exert a force upon the flexible membrane so as to operably reduce the second volume of the catheter, thereby unloading the desired volume of the drug into the target of interest.

Moreover, the method may also include scanning tissue of the human or the animal to acquire, store and process a 3D reference of tissue prior to the tissue being surgically exposed, so as to create a triangularized mesh based on the scanned tissue, determine the volumetric center of a particular portion of the tissue to be ablated, coagulated or medicated during the surgery, and implement an algorithm using the triangularized mesh and the physical space data collected by the instrument to determine the point-based registrations.

Preferably, the image-guided surgical procedure is performed by transmitting a free electron laser (FEL) to surgically ablate a particular portion of a tissue.

Preferably, the magnetic tracking tip location data comprises {x, y, z} positional coordinates and orientation angles and a rotation matrix, wherein the image space comprises scanned images that are preoperatively obtained.

In another aspect, the invention relates to an apparatus for performing an image-guided surgical procedure with an instrument in a target of interest of a human or an animal and delivering a desired volume of a drug therein during the image-guided surgical procedure. In one embodiment, the apparatus includes an endoscope as disclosed above, a magnetic tracking system configured to detect the magnetic tracking tip in a 3D physical space and an image data processor.

Preferably, the image data processor is configured to obtain an image space having a plurality of tomographic images each containing all image information; determine point-based registrations mapping the 3D physical space to the image space based on points in the 3D physical space and corresponding points in the image space; determine a location and an orientation of the instrument in the image space based on magnetic tracking tip location data generated by the magnetic tracking tip in the 3D physical space and the point-based registrations; and dynamically display, while performing the image-guided surgical procedure, a selected one of the plurality of the tomographic images that overlaps the location of the instrument in the image space and indications of the location and orientation of the instrument in the image space.

Preferably, the instrument is configured to transmit an FEL that surgically ablates a particular portion of a tissue, and comprises a laser delivery system including a waveguide and a lens mounted to a distal end of the waveguide adjacent to the distal end of the endoscope, wherein a proximal end of the waveguide is coupled to a laser source.

In addition, the apparatus also includes a scanning device for scanning tissue of the patient to acquire, store and process a 3D reference of tissue prior to the tissue being surgically exposed, wherein the image data processor creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations.

For the magnetic tracking system, the image data processor and the scanning device of the apparatus, and the image-guided surgical procedure performed with the apparatus, please refer to U.S. patent application Ser. No. 13/848,505, which is incorporated herein in its entirety by reference, for the details.

Figure 3:
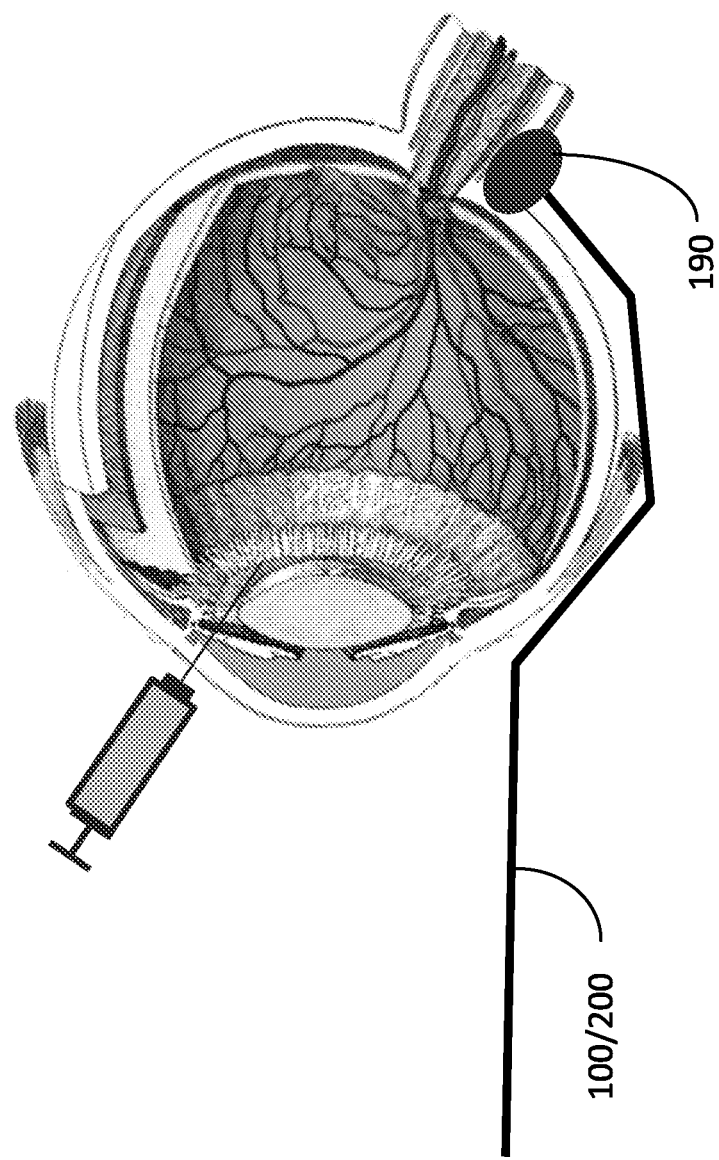
FIG. 3 shows a drug delivery at a rear optic nerve back of an eye in the image-guided surgical procedure according to one embodiment of the invention.

With the image guidance systems, when one has the ability to reach target points, usually, the target points are resected or ablated. But in some cases, e.g., the eye, one may want to inject a fluid, such as drug, chemotherapy agent, and the likes. The problem is that doing that remotely means difficulty in controlling amount delivered and a large amount of wastage if you fill the delivery catheter entirely with the delivery fluid. However, according to the invention, a precise amount of the drug can be delivered to the target, by applying, during or after the image-guided surgical procedure, a pressure into the first volume of the catheter to exert a force upon the flexible membrane, which operably squeeze the second volume of the catheter and invert the flexible membrane. FIG. 3 shows such a drug delivery at a rear optic nerve back of an eye in the image-guided surgical procedure, by applying the method with the apparatus having the endoscope 200 that utilizes the drug delivery device 100.

The above described embodiments of the drug delivery device 100 use a small tube/catheter 110 with an internal membrane 120 to be inserted through a working channel of an endoscope into the retro-orbital space of a patient or animal. Such an endoscope has to be small necessitating an even smaller working channel and thus a small delivery catheter/tube. In such a scenario 0.5-1.5 mm diameter delivery tube, the surface tension is more than adequate to hold the drug volume in the space defined by the interior surface of the tube and the membrane of the drug delivery device.

However, in certain embodiments, one may scales up the endoscope and proportionally scale the working channel and the delivery tube/catheter. As such, surface tension alone might not retain the drug volume. In addition, recent medical events have raised issues about the sterility of scopes even after approved cleaning. Therefore it may be desired to place a barrier between the preloaded drug (fluid) volume and the working channel. In one embodiment, the preload drug volume is protected by placing an adhesive cover over the distal end of the delivery catheter/tube.

In certain embodiments, as shown in FIGS. 4D-4F, the drug delivery device 300 or 400, which is essentially similar to the drug delivery device 100 shown in FIGS. 1-2, except that a retention cap 140 is attached to the distal end (tip) 114 of the delivery catheter/tube 110 to protect the preload drug volume 190. In certain embodiments, the retention cap 140 is attached to the distal end 114 of the delivery tube 110 by gluing, or by other attaching means, e.g., but is not limited to, threading, or welding. In practice, the retention cap 140 can be attached to the outer surface of the delivery tube 110 at the distal end 114 of the delivery tube 110, as shown in FIGS. 4D and 4E, or the inner surface of the delivery tube 110 at the distal end 114 of the delivery tube 110, as shown in FIG. 4F.

In certain embodiments, the retention cap 140 can be made of a stiff, waterproof material with a known elastic limit. In one embodiment, as shown in FIGS. 4A-4C, the retention cap 140 has an trough 141 that is either molded or cut into its surface at an arc of about 300°-350°, an operably openable surface 142 defined by the trough 141 and a hinge 145. Operably, when the surface 142 is opened and hinged at the hinge 145, it defines an opening 143 in the retention cap 140, as shown in FIGS. 4B and 4E. When the preload fluid/drug volume 190 behind the retention cap 140 is pressurized from the first volume 111 of the catheter 110 to exert a force upon the flexible membrane 120 to squeeze the second volume 113 of the catheter 110, the operably openable surface 142 of the retention cap 140 is ruptured along the thin trough 141, and hinged at the hinge 145. The preload fluid/drug volume 190 is then unloaded/released into the target of interest through the opening 143 of the retention cap 140. In certain embodiments, the retention cap 140 is a very thin cap, and the opening 143 has a diameter that is substantially the same as an inner diameter of the delivery catheter/tube 110. Accordingly, the preload fluid/drug volume 190 can be unloaded/released completely by inverting the flexible membrane 120. In addition, the hinge 145 is adapted to prevent the ruptured surface 142 from leaving the retention cap 140 when unloading/releasing the preload fluid/drug volume 190.

Since the pressure to rupture the retention cap 140 is transmitted by the fluid, this works in the scenario where the membrane 120 is designed not to exceed to the tip 114 of the delivery tube 110 or in those cases where it may.

Similar to the drug delivery device 100 shown in In FIG. 1, for the drug delivery device 300 shown in FIGS. 4D-4E, or 400 shown in FIG. 4F, no flow regulator is needed, since the amount of the drug delivered is known. In other words, the drug delivery device 300 or 400 according to embodiments of the invention is also devoid of a flow regulator for regulating a flow of the desired volume of the drug into the target of interest, which makes the device design simple, improves the operability and reduces the cost.

In addition, one aspect of the invention is also directed to a novel image guided endoscope that utilizes the above-disclosed drug delivery device 300 or 400. Operably, the image guided endoscope is substantially the same as the image guided endoscope 200 utilizing the drug delivery device 100. For the details of the image guided endoscope, please refer to the above description of the image guided endoscope 200, which will not be repeated herein.

In another aspect, the invention relates to an apparatus for performing an image-guided surgical procedure with an instrument in a target of interest of a human or an animal and delivering a desired volume of a drug therein during the image-guided surgical procedure. In one embodiment, the apparatus includes an endoscope as disclosed above, a magnetic tracking system configured to detect the magnetic tracking tip in a 3D physical space and an image data processor. Please refer to the above description of the apparatus for the details, which will not be repeated herein.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A drug delivery device for delivering a desired volume of a drug into a target of interest of a human or an animal, comprising:
   (a) a catheter having a first end and an opposite, second end, being slidable into a guidance device;
   (b) a retention cap attached to the second end of the catheter, having an operably openable surface and a hinge;
   (c) a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable; and
   (d) a pressurizable member coupled to the catheter for operably changing the first volume and the second volume of the catheter,
   wherein the drug delivery device is devoid of a flow regulator for regulating a flow of the desired volume of the drug into the target of interest; and
   wherein in use, the desired volume of the drug is preloaded into the second volume of the catheter that in turn is slid into the guidance device, and when the guidance device is placed in the target of interest, the pressurizable member applies a pressure into the first volume of the catheter to exert a force upon the flexible membrane so as to operably reduce the second volume of the catheter, which in turn pressurizes the operably openable surface of the retention cap to open, thereby unloading the desired volume of the drug into the target of interest.

2. The drug delivery device of claim 1, wherein the first volume of the catheter is filled with fluid comprising benign gas or liquid.

3. The drug delivery device of claim 2, wherein the fluid comprises saline.

4. The drug delivery device of claim 1, wherein the flexible membrane is made of an elastic material that is compatible with both the fluid in the first volume and the preloaded drug in the second volume.

5. The drug delivery device of claim 1, wherein the flexible membrane is impermeable to both the fluid in the first volume and the preloaded drug in the second volume.

6. The drug delivery device of claim 1, wherein the catheter is rigid or flexible.

7. The drug delivery device of claim 1, wherein the retention cap has an operable opening defined when the operably openable surface is operably opened and hinged at the hinge, wherein the operably opening has a diameter that is substantially the same as an inner diameter of the catheter.

8. The drug delivery device of claim 1, wherein the retention cap has an trough that is either molded or cut into its surface to define the operably openable surface and the hinge.

9. The drug delivery device of claim 1, wherein the retention cap is attached to an outer surface of the second end of the catheter, or an inner surface of the second end of the catheter.

10. The drug delivery device of claim 1, wherein the pressurizable member comprises a syringe coupled to the first end of the catheter and being in a fluid communication with the first volume of the catheter.

11. The drug delivery device of claim 1, wherein the guidance device comprises an endoscope.

12. The drug delivery device of claim 1, being disposable or re-useable.

13. An endoscope, comprising:
(a) a probe housing having a proximal end, a distal end and a lumen extending between the proximal end and the distal end;
(b) at least one image fiber disposed in the lumen that communicates image information from the distal end of the probe; and
(c) a drug delivery device for delivering a desired volume of a drug into a target of interest, comprising:
  (i) a catheter disposed in the lumen, having a first end close to the proximal end of the probe, and an opposite, second end close to the distal end of the probe;
  (ii) a retention cap attached to the second end of the catheter, having an operably openable surface, a hinge and an operable opening defined when the operably openable surface is operably opened and hinged at the hinge;
  (iii) a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable, wherein the desired volume of the drug is preloaded into the second volume of the catheter; and
  (iii) a pressurizable member coupled to the first end of the catheter for operably unloading the desired volume of the drug into the target of interest,
  wherein the drug delivery device is devoid of a flow regulator for regulating a flow of the desired volume of the drug into the target of interest; and
(d) an access conduit disposed in the lumen that receives an ablation instrument or a coagulating instrument for performing a surgical procedure.

14. The endoscope of claim 13, wherein the first volume of the catheter is filled with fluid comprising benign gas or liquid.

15. The endoscope of claim 13, wherein the flexible membrane is made of an elastic material that is compatible with both the fluid in the first volume and the preloaded drug in the second volume.

16. The endoscope of claim 13, wherein the flexible membrane is impermeable to both the fluid in the first volume and the preloaded drug in the second volume.

17. The endoscope of claim 13, wherein the retention cap has an operable opening defined when the operably openable surface is operably opened and hinged at the hinge, wherein the operably opening has a diameter that is substantially the same as an inner diameter of the catheter.

18. The endoscope of claim 13, wherein the retention cap has an trough that is either molded or cut into its surface to define the operably openable surface and the hinge.

19. The endoscope of claim 13, wherein the retention cap is attached to an outer surface of the second end of the catheter, or an inner surface of the second end of the catheter.

20. The endoscope of claim 13, wherein the pressurizable member comprises a syringe coupled to the first end of the catheter and being in a fluid communication with the first volume of the catheter.

21. The endoscope of claim 13, wherein in use, during the surgical procedure, the pressurizable member applies a pressure into the first volume of the catheter to exert a force upon the flexible membrane so as to operably reduce the second volume of the catheter, which in turn pressurizes the operably openable surface of the retention cap to open, thereby unloading the desired volume of the drug into the target of interest.

22. The endoscope of claim 13, further comprising:
a magnetic tracking tip disposed proximate the distal end of the probe housing and configured to generate magnetic tracking tip location data identifying a location of the distal end of the probe housing.

23. The endoscope of claim 13, further comprising:
a purge fluid/gas port disposed at the proximal end of the flexible probe that accepts purge fluid/gas; and
a purge fluid/gas conduit disposed in the lumen and in fluid communication with the purge fluid/gas port, the conduit delivering purge fluid/gas to the distal end of the endoscope.

24. The endoscope of claim 13, wherein the ablation instrument is a laser delivery system comprising:
(a) a waveguide disposed in the lumen;
(b) a laser source coupled to a proximal end of the waveguide; and
(c) a lens mounted to a distal end of the waveguide nearest the distal end of the endoscope.

25. The endoscope of claim 13, wherein the ablation instrument uses one of radio-frequency waves, microwaves, ultrasonic waves, infrared waves, heat, cryoablation, and a laser to ablate the particular portion of the tissue.

26. The endoscope of claim 13, wherein the coagulating instrument uses one of radio-frequency waves, microwaves, ultrasonic waves, infrared waves, heat, cryoablation and a laser.

27. An apparatus for performing an image-guided surgical procedure with an instrument in a target of interest of a human or an animal and delivering a desired volume of a drug therein during the image-guided surgical procedure, comprising:
(a) an endoscope comprising:
(i) a probe housing having a proximal end, a distal end and a lumen extending between the proximal end and the distal end;
(ii) at least one image fiber disposed in the lumen that communicates image information from the distal end of the probe; and
(iii) a drug delivery device comprising:
a catheter disposed in the lumen, having a first end close to the proximal end of the probe, and an opposite, second end close to the distal end of the probe;
a retention cap attached to the second end of the catheter, having an operably openable surface and a hinge;
a flexible membrane having a rim securely connected to an inner surface of the catheter at a position proximal to the second end of the catheter to define a first volume inside the catheter between the first end and the flexible membrane, and a second volume inside the catheter between the flexible membrane and the second end, such that the second volume is substantially the same as the desired volume of the drug, wherein the first volume and the second volume are operably and complementally changeable, wherein the desired volume of the drug is preloaded into the second volume of the catheter; and
a pressurizable member coupled to the first end of the catheter for operably unloading the desired volume of the drug into the target of interest,
wherein the drug delivery device is devoid of a flow regulator for regulating a flow of the desired volume of the drug into the target of interest; and
(iv) an access conduit disposed in the lumen that receives the instrument; and
(v) a magnetic tracking tip disposed proximate the distal end of the probe housing and configured to generate magnetic tracking tip location data identifying a location of the distal end of the probe housing;
(b) a magnetic tracking system configured to detect the magnetic tracking tip in a three dimensional (3D) physical space; and
(c) an image data processor configured to obtain an image space having a plurality of tomographic images each containing all image information;
determine point-based registrations mapping the 3D physical space to the image space based on points in the 3D physical space and corresponding points in the image space;
determine a location and an orientation of the instrument in the image space based on magnetic tracking tip location data generated by the magnetic tracking tip in the 3D physical space and the point-based registrations; and
dynamically display, while performing the image-guided surgical procedure, a selected one of the plurality of the tomographic images that overlaps the location of the instrument in the image space and indications of the location and orientation of the instrument in the image space.

28. The apparatus of claim 27, wherein the instrument is configured to transmit a free electron laser (FEL) that surgically ablates a particular portion of a tissue, and comprises a laser delivery system including a waveguide and a lens mounted to a distal end of the waveguide adjacent to the distal end of the endoscope, wherein a proximal end of the waveguide is coupled to a laser source.

29. The apparatus of claim 27, wherein the magnetic tracking tip location data comprises {x, y, z} positional coordinates and orientation angles and a rotation matrix, wherein the image space comprises scanned images that are preoperatively obtained, wherein the image data processor provides the scanned images for display while the image-guided surgery is being performed.

30. The apparatus of claim 27, wherein in use, during the image-guided surgical procedure, the pressurizable member applies a pressure into the first volume of the catheter to exert a force upon the flexible membrane so as to operably reduce the second volume of the catheter, thereby unloading the desired volume of the drug into the target of interest.

31. The apparatus of claim 27, further comprising:
a scanning device for scanning tissue of the patient to acquire, store and process a 3D reference of tissue prior to the tissue being surgically exposed, wherein the image data processor creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations.

* * * * *